United States Patent [19]

Evans

[11] 4,151,304
[45] Apr. 24, 1979

[54] METHOD AND COMPOSITION FOR MOISTURIZING THE SKIN

[75] Inventor: Anthony Evans, Teaneck, N.J.

[73] Assignee: Lever Brothers Company, New York, N.Y.

[21] Appl. No.: 739,374

[22] Filed: Nov. 5, 1976

[51] Int. Cl.$^2$ .......................... A61K 7/00; A61K 7/40; A61K 7/42; A61K 7/44

[52] U.S. Cl. ...................................... 424/361; 424/59; 424/60; 424/180; 424/362; 424/365; 536/119

[58] Field of Search ..................... 424/49, 59, 60, 180, 424/361, 362, 365; 536/119

[56] References Cited

U.S. PATENT DOCUMENTS 3,849,341  11/1974  Lamberti .............................. 252/546

FOREIGN PATENT DOCUMENTS 49-11994  3/1974  Japan.

OTHER PUBLICATIONS

Okahara, Chem. Abs, vol. 59, 1963, pp. 12892–12893.

Conrad, Cos & Perf, vol. 89, Mar. 1974, pp. 33–34, 63–64.
Robinette, Chem. Abs, vol. 81, 1974, Ab No. 82219n.
Boublik, Chem. Abs, vol. 81, 1974, Ab No. 41295r.

*Primary Examiner*—Anna P. Fagelson
*Attorney, Agent, or Firm*—Michael J. Kelly; James J. Farrell; Melvin H. Kurtz

[57] ABSTRACT

The use of certain complex carboxylic acids and the salts thereof in compositions capable of providing a moisturizing effect in skin and methods for their use is disclosed. The compositions comprise a water-in-oil emulsion containing an amount that is effective to provide a moisturizing effect when applied to the skin, of a compound selected from the group consisting of α-methyl-butyrolactone-γ-carboxylic acid, the alkali metal salts of said acids and mixtures thereof; or selected from the group consisting of the succinic half acid esters of sucrose having a degree of substitution of at least about 5, the salts of said acids and mixtures thereof.

9 Claims, No Drawings

METHOD AND COMPOSITION FOR MOISTURIZING THE SKIN

BACKGROUND OF THE INVENTION

Field Of The Invention

The present invention relates to skin moisturization and more specifically, to compositions capable of imparting a moisturizing effect to the skin and methods for their use.

Physiologically, the skin is an organ composed of several layers, of tissue, the most external of which is called the stratum corneum. Underlying the stratam corneum is a basal layer which in turn is followed by a layer known as the dermis. The entire skin organ functions as a primary moisture reservoir for the body as well as a protective mantle.

The outermost layer, the stratam corneum, varies in thickness from about 15 microns to about 500 microns depending upon body location. The thinnest layer is usually associated with the face or the back of the hands while the thickest layers are associated with gripping or walking surfaces, i.e. the palms of the hands or the soles of the feet. This layer plays its most significant role in controlling the level of moisture in the skin and is composed of keratinized cells, a natural moisturizing factor, and lipids. All of these function together as a protective coating, as well as a moisture barrier to retain moisture within the skin.

The cells of the basal layer undergo systematic change from the normal cell structure to the keratinized layer of the corneum. During this change, biochemical protein breakdown products are formed, among which are pyrrolidone carboxylic acids, which are believed to function as natural moisturizing compounds. Below the basal layer lies the normal dermis of the skin that holds and serves as the transport means for water to the general area.

Water is extremely important to the proper physical condition and appearances of the skin. Dry and chapped skin is largely the result of an insufficient level of moisture in the stratum corneum. Dry skin is usually characterized by at least one of the following signs or symptoms:

(a) rough and flaky appearance,
(b) reduced flexibility, or
(c) surface fissures.

As previously stated, not all of the signs or symptoms need be present simultaneously and it is quite common for skin to be rough and flaky while still retaining normal flexibility, or the skin may be able to retain a smooth surface with concurrent loss of flexibility. Both conditions could be due to lack of moisture in the outermost layer. While dry skin is characterized by the above signs, their presence does not preclude other causes which could be the underlying cause of the condition. In general, however, soft, pliable and healthy skin cannot be maintained in the absence of the proper level of moisture in the stratum corneum.

The leverl of moisture in the skin is dependent upon a number of factors among which are the water binding potential of the stratum corneum, the rate at which water is supplied to the internal layers of the stratum corneum, and the rate at which water is lost from the skin via external evaporation. Under normal conditions the water content and vapor pressure of the epidermis are higher than those of the surrounding air which results in the evaporation of water from the skin surface. Replenishment of this lost water is normally carried out by the body; however, the ability to replenish this water diminishes with age resulting in the general loss of skin softness and pliability with maturation. Additionally, skin can become dry because of excessive loss of water due to exposure to low humidities, continuous use of soaps or detergents, and contact with solvents or anhydrous materials. With these factors in mind, investigators have for a long time been actively searching for ways to maintain proper levels of moisture in the skin.

Historically, formulations can be traced back to the second century for a cream named "Ceratum Galeni" which comprises a mixture of molten bees wax and perfumed olive oil in which was incorporated the maximum quantity of water. More recent classical examples of emollient creams include the USP (United States Pharmacopiea) "Unguentum Aquae Rosae." This mixture's composition was reported as early as 1820 to contain about 45 percent rosewater, 40 percent expressed almond oil, 12 percent spermaceti and 3 percent bees wax. A general treatment of this historical development of skin care treatment products can be found in *Cosmetics Science and Technology;* Sagarin et al.; Interscience Publishers, Inc.; New York, New York; 1957, pages 81-182 which are incorporated herein by reference.

Since there appears no doubt that the water content of the stratum corneum is a very important factor in maintenance of normal soft flexible skin, most efforts have been directed to means for replenishment of this water from an external source. The treatment of dry skin involves the use of basic ingredients that have come to be known as emollients. Although the term has gained wide application, an emollient is generally defined as an agent which when applied to the skin will effect a softening of dry inflexible corneum by inducing rehydration.

While the evidence points to the fact that water alone might suffice as a treatment agent there has been great difficulty in achieving any significant result via this agent alone. The difficulty arises in the application itself since only a very thin film of water can be made to adhere to the skin. Due to the competing physical forces, evaporation will take place before any emollient effect can take place. Prolonged immersion in large quantities of water to overcome the problem of evaporation presents the danger of over hydration resulting in swelling of the corneum, possible cellular damage and even exacerbation of the original condition.

These problems have been overcome by incorporating water in various cosmetically acceptable bases that will allow availability of water to the stratum corneum and regulate water take-up. A presentation of examples of the kinds of compositions that have been developed is set forth in *Cosmetics Science and Technology,* Supra.

While many of the raw materials employed in these formulations possess emollient potential, the ingredients are usually classified on the basis of the particular feature of that ingredient in the overall formulation. In general the catagories comprise:

| | |
|---|---|
| 1. Emollients | 5. Emulsifiers |
| 2. Barrier Agents | 6. Preservatives |
| 3. Healing Agents | 7. Perfume Oils |
| 4. Humectants | 8. Coloring Agents |

Humectants were originally employed to control moisture exchange between the product and the air, both in storage and on the skin. The earliest of hand-treatment products, "glycerine and rosewater", was simply a mixture of humectant (the glycerine) and water (the rosewater). While many agents posses sufficient humectant properties to ensure against water loss in the product, only three have found wide acceptance in commercial skin preparations. These include glycerol, propylene glycol, and sorbitol. The compounds are similar in that they are all polyhydric alcohols; however, their behavior in skin care products is quite dissimilar.

While the ability to prevent drying of the preparation itself may be important for aesthetic reasons such as consumer acceptance, it is more desirable to incorporate humectants that also possess the ability to impart an emollient effect. It should be noted that the presence or ability of the humectant to stabilize the formula, i.e., prevent water loss from the composition, is not indicative or anticipatory of an emollient effect on the skin by the same agent.

Typical humectants used in the past did decrease the rate of water loss from the vehicle itself and did prevent crust formation; however, they did not do one of two things: decrease the rate of water loss from, or increase the water content of, the stratum corneum.[1]
1. Shelmire Jr., J. B.; "Archives of Dermatology," 82:24-31, 1960.

DISCUSSION OF RELATED ART

Lewis, U.S. Pat. No. 3,016,334 discloses a skin cream for topical cosmetic application comprising a water-in-oil emulsion providing a cream base wherein the water phase contains a low gel strength, low viscosity, gelatin derived from collagen protein as an active agent and reported to be instrumental in enhancing the absorbtion of water by the skin.

Laden, U.S. Pat. No. 3,235,457 discloses closely related hygroscopic salts of certain carboxylic acids as having humectant properties.

Nieper et al. U.S. Pat. No. 3,274,063 discloses certain water-in-oil cosmetic preparations containing magnesium asparaginate for the purpose of imparting smooth skin to the user.

Friedman et al. U.S. Pat. No. 3,932,622 discloses a skin moisturizing composition capable of providing a "super-moisturizing effect" comprising a water-in-oil emulsion of the dialkali metal salt of N-acetyl glutamic acid.

Rieger et al. J. Soc. Cosmet. Chem. 25, 253-262, in a discussion of cosmetic ingredient effects on stratum corneum, discloses the effect of sodium pyrrolidone carboxylate on the elastic modulus and relaxation modulus of treated skin.

While the art discloses various solutions to the dry skin problem, the compounds of the prior art, unfortunately, provide relatively expensive alternatives since the compounds disclosed require ingredients that are difficult to synthesize and are prohibitively expensive in retain formulations. Applicant has now discovered that adequate moisturization can be achieved using compounds that are easy and economical to produce.

SUMMARY OF THE INVENTION

An object of the instant invention is to provide a cosmetic composition which will provide a moisturizing effect when applied to the skin.

Another object of the instant invention is to provide a moisturizing cosmetic composition which will provide a moisturizing effect over extended periods of time when applied to the skin.

These, and other objects that will be made apparent in the detailed description to follow, are accomplished according to the present invention by providing for a moisturizing composition comprising a water-in-oil emulsion and an amount which is effective to provide a moisturizing effect of a compound selected from the group consisting of α-methyl-butyrolactone-γ-carboxylic acid, an alkali metal salt of said acid and mixtures thereof; or a compound selected from the group consisting of a succinic half acid ester of sucrose, an alkali metal salts of said acid and mixture thereof.

DETAILED DESCRIPTION OF THE INVENTION

The instant invention is based upon the discovery that stratum corneum can be caused to uptake a significant amount of water and thereby demonstrate a skin moisturizing effect when that tissue is treated with α-methyl-butyrolactone-γ-carboxylic acid, a succinic half acid ester of sucrose, an alkali metal salt of those acids or mixtures thereof or mixtures of the different salt of said acids. The α-methyl-butyrolactone-γ-carboxylic acid and its salts, hereinafter referred to as the "lacto acids" and "lacto salts" for the purpose of convenience are of the general formula:

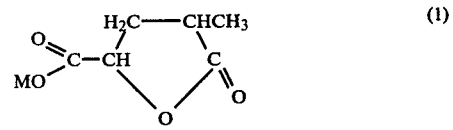

wherein M may be hydrogen, sodium or potassium.

The succinic half acid esters of sucrose and their salts, hereinafter referred to as the "ester acids" and the "ester salts" respectively for the purpose of convenience, are of the general formula:

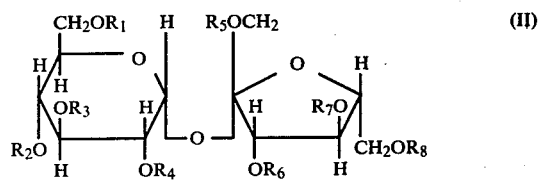

wherein $R_1$, $R_2$, $R_3$, $R_4$, $R_5$, $R_6$, $R_7$, and $R_8$, each, may be either hydrogen; or are of the general formula

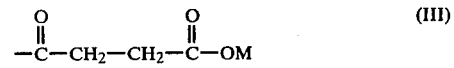

wherein M is hydrogen, sodium, or potassium; and mixtures thereof, and wherein the average degree of esterfication is at least about 62 mole percent [i.e., a degree of substitution (D.S.) of at least about 5].

It has been surprisingly discovered that this narrowly defined group of compounds are highly effective when applied to the stratum corneum in the form of a composition comprising an effective amount of the compound to provide a moisturizing effect, and a suitable cosmetic base including but not limited to lotions, creams and in particular water-in-oil emulsions. By suitable cosmetic base is meant a vehicle that provides the means for applying the compound to the skin and which will not substantially interfere with the efficacy of the compound in its moisturizing effect.

While not wishing to be bound by the foregoing statement, applicant presently believes that the ability of these compounds to bind water in the stratum corneum is due to their molecular configuration especially in the ionized form. While it is preferred to employ the compounds in their salt form, it is possible to employ the free acid forms since the free acid will rect with sources of alkali metal ions naturally present on the skin or in perspiration therefrom to form the respective salt after their application to the skin.

The α-methyl-butyrolactone-γ-carboxylic acid, and in particular the sodium salt thereof, can be prepared by the procedure as set forth in British Pat. No. 995,349, issued to Mitsubishi Chemical Industries Limited, on June 16, 1965. The materials tested in connection with the instant invention were prepared by two alternative procedures. In the first, 180g of a 80 percent solution of lactic acid was reacted with a sufficient amount of KOH to convert the lactic acid to a potassium salt. An additional 30 grams of KOH and 3g of ZnO were then added to the resulting solution and the mixture was transferred to a liter Parr Bomb. The mixture in the bomb was brought to a temperature of 230° C. and was maintained there for about 6 hours. After cooling, the contents of the bomb were dissolved in water and were then acidified with a sufficient amount of HCl. The resulting solution was then concentrated by evaporation to yield a residue. To the residue, now contained in a flask, was added 200 ml of ethyl alcohol, 600 ml of benzene, and 3 ml of concentrated $H_2SO_4$. The flask was then fitted with a Dean-Stark trap and the solution was heated at reflux until the formation of water ceased. The contents of the reflux mixture was then washed with a solution of $Na_2CO_3$ which was followed by several water washings until the wash water was found to be neutral by pH paper. The resulting solution was then dried, concentrated and fractionally distilled (b.p. 130°–132° C. at 5.5 mm Hg). The resulting diester was then subjected to acid hydrolysis and the resulting lactone acid was converted to the monosodium salt by the addition of sufficient NaOH.

Alternatively, the compound was also synthesized by dissolving 1.2g (0.05 moles) of sodium metal in 100 ml of anhydrous methanol. To this solution was added with stirring 53g (0.4 moles) of dimethyl malonate. To the resulting solution, 20g (0.2 moles) of methyl methacrylate was added and the solution was heated at reflux with stirring for about 3½ hours. After the solution had been allowed to cool, it was transferred to a separatory funnel along with about 300 mls of ethyl ether. This solution was then extracted with a saturated NaCl solution until the extract was neutral to pH paper. The contents of the separatory funnel were then dried, concentrated and were ultimately fractionally distilled (b.p. 123°–125° C. at 3.5 mm Hg). This fraction was then brominated in $CCl_4$ in the presence of light which was followed by acid hydrolysis. The resulting lactone acid was treated with a sufficient amount of NaOH to yield the compound in the corresponding salt form.

It should be noted that the lacto salts and lacto acids can be prepared by various other means and with considerable variation in technique.

The succinic half acid esters are produced, among other ways, from the reaction of sucrose in the presence of pyridine with succinic anhydride. The reaction generally produces a mixture of variously substituted forms and the average degree of substitution can easily be determined via titration. The average degree of substitution can be controlled by variation of the ratios of the reactants, or fractions of certain average substitution can be separated from a general reaction mixture by standard techniques by one skilled in the art. In one preparation of the ester salts 25g (0.073 moles) of sucrose was added to 125 mls of pyridine in a reflux flask. The mixture was heated at reflux for a period of ½ hour whereupon 65g (0.65 moles) of succinic anhydride was added to the mixture and heating at reflux was continued for 2 hours. The resulting reaction mixture was then concentrated to yield a viscous residue which was then dissolved in water. About 69g (0.65 moles) of $Na_2CO_3$ was then gradually added to this solution. Upon completion of this addition the solution was freeze dried whereupon the resulting dry material was extracted with anhydrous methanol with removal of insolubles by filtration. The sucrose succinates were then precipitated from the methanol by the addition of acetone and separated by filtration.

Again as with the lacto salts and acids the ester acids and salts can be produced in various ways, and manner of preparation is not material to the application of the compounds in the instant invention. As previously, mentioned, various degress of substitution or esterfication can be expected and the resulting mixtures can be characterized by titration. For the purpose of discussion, particular mixtures will be characterized by the average degree of substitution. Thus a D.S. (degree of substitution) value of 2 will indicate an average of 2 moles of succinate esterfication per mole of sucrose while a D.S. value of 0.5 will be indicative of an average of ½ of succinate esterfication per mole of sucrose. In general, this invention is directed to ester acids and salts having D.S. values of at least about 5 or about 62 mole percent substitution.

These compounds are employed in the cosmetic composition in an amount which is effective to moisturize the skin. Typically, they will be employed in amounts greater than about one percent by weight of the composition. Preferably, they are employed in an amount from about 2 percent to about 10 percent, and more preferably from about 2 percent to about 5 percent. Combinations of the acids and their respective salts are contemplated within the amount effective to moisturize the skin.

The compounds can be combined with other emollient ingredients including but not limited to such things as wax esters such as lanolin, spermaceti and beeswax; steroid alcohols such as cholesterol and lanolin alcohols; fatty alcohols such as lauryl, cetyl, oleyl and stearyl alcohols; triglyceride esters; phospholipids such as lecithin and cephalin; polyhydric alcohol esters such as mono- and di-fatty acid esters of ethylene cylcol, diethylene glycol, polyethylene glycols, propylene glycols, glycerol, sorbitol, sorbitan, mannitol, pentaerythritol, polyoxyethylene sorbitol and polyoxyethylene sorbitan; fatty alcohol ethers such cetyl, stearyl, or oleyl clycol, of ethylene oxide polymers; alkyl fatty esters such as methyl, isopropyl and butyl esters of fatty acids; hydrocarbon oils and waxes such mineral oil, petrolatum and paraffin; hydrophillic lanolin derivatives such as polyoxyethylene sorbitol lanolin and polyoxyethylene lanolin derivatives; hydrophilic beeswax derivatives such as polyoxyethylene sorbitol beeswax; and silicone oils such as dimethyl polysiloxanes and mixed methyl phenyl polysiloxanes.

Additionally, barrier agents can be combined in the cosmetic vehicle which when incorporated into the composition and then applied to the skin will act as barriers to external insults from potential skin irritants. These barrier agents include, for example, but are not limited to petrolatum, paraffin wax, ozokerite wax, vegetable waxes, beeswax, casein, methyl cellulose, sodium carboxymethyl cellulose, ethylcellulose, cellulose acetate butyrate, nitrocellulose, alginic acid salts and derivatives, zein, tragacanth, pectin, quince, seed gel, bentonite, zinc oxide, zince stearate, sodium silicate, talc, stearic acid, titanium dioxide, and silicones.

Healing agents to stimulate the growth of healthy granulation tissue is also contemplated within the scope of the cosmetic vehicle. These agents include for example urea allantoin.

Also contemplated within the scope of the cosmetic vehicle are various humectants to control the moisture exchange between the product and air both in its package and on the skin. These humectants include, but are not limited to, such things as glycerol, propylene glycol and sorbitol.

Other ingredients serving only to make the product more attractive to the user and to improve storage ability can also be employed in the cosmetic vehicle. These include such things as emulsifiers, preservatives, perfume and coloring agents.

Emulsifiers contemplated can be classified into three major catagories anionic, cationic, and nonionic. Anionic emulsifiers include for example such things as fatty acid soaps, polyol fatty acid mono esters containing fatty acid soaps, sulfuric esters and polyol fatty acid monoesters containing sulfuric esters. Cationic emulsifiers include for example such things as N(stearoyl colamino formylmethyl)pyridinium chloride, N-soya-N-ethyl morpholinium ethosulfate, alkyl dimethyl benzyl ammonium chloride, (Diisobutyl phenoxy ethoxy) ethyl dimethyl benzyl ammonium chloride, and cetyl pyridinium chloride. Nonionic emulsifiers include for example polyoxyethylene fatty alcohol ethers, polyoxyethylene fatty acid ester, polyoxyethylene sorbitan fatty acid esters, sorbitan fatty acid esters, polyoxyethylene glycol fatty acid esters and polyol fatty acid esters.

Examples of preservatives include benzoic acid, sodium benzoate, sodium propionate, salicylic acid and the ethyl, propyl, and butyl esters of hydroxybenzoic acid.

The moisturizing cosmetic composition of the instant invention can be in the form of a lotion or a cream; whatever the form, however, it will generally comprise an emulsion of water and oil. These formulations can be prepared from bases well known in the art by combining these bases with the compounds of the instant invention to produce the novel compositions. The most successful applications include, however, specifically those bases employing a water-in-oil emulsion. The use of the water-in-oil emulsion is believed necessary to obtain a significant moisturizing effect. This emulsion should contain a ratio of water-to-oil of from between about 1:20 to about 20:1. Preferably the water-to-oil ratio will be within the range of from about 1:2 to about 3:1, and more preferably from about 1:1 to about 2:1. The selection of the exact water-in-oil ratio and the emulsifier system employed will depend upon the type of product desired, e.g. whether it is to be a lotion or a cream and what the viscosity and feel should be. An added advantage of the present invention is that the water-in-oil emulsions prepared in accordance with the teachings herein are less viscous, greasy or oily in feel than otherwise and are, therefore, more suitable for cosmetic use.

It is usually desirous to employ at least one emulsifier, alone or in combination with other emulsifiers, capable of producing a shelf-stable water-in-oil emulsion. However, such stability is only necessary for consumer appeal and is not paramount for product effectiveness. Typical of the emulsifiers which can be employed are beeswax/borax, lime water/stearic acid, sorbitan trioleate, sorbitan sesquioleate, oleth-2, and cholesterol absorption base. A preferred emulsifier system comprises beeswax/borax and lime water/stearic acid at a level of about 4% by weight of the emulsion. These and the other emulsifiers can be employed at any level effective to form a suitably stable emulsion. The exact levels are easily determinable by those skilled in the art.

The oil phase of the emulsion will typically comprise known oils acceptable for cosmetic use among which are the animal, vegetable, and mineral oils. With these, also in the oil phase, a number of other compounds can be employed to modify the texture, feel, rub-in, after-feel, viscosity, and other physical attributes of the product. For example, waxes can be added to increase texture, and lanolin emulsifiers can be added to modify product texture and skin feel. Further, such materials as lanolin alcohols can be added for their known special textural and tactile effects on the skin.

The water phase of the emulsion contains the water and the water soluble components of the composition. Preferably, the water is employed as saturated lime water; with calcium chloride sometimes being added to assure satisfactory stability to the water-in-oil emulsion. Also present in the water phase may be water soluble or dispensible materials which can be added for the purpose of adjusting the physical properties of the emulsion during processing or in final form.

In preparing the emulsion, the oil and the water phases are both prepared separately and then combined with vigorous agitation to effect emulsification. The oil phase can be prepared in known manner, such as melting and blending the ingredients to form a uniform phase. The water phase is also prepared in known manner, such as simply mixing until all of the soluble materials are dissolved. The oil and water phases are admixed and blended in the liquid state. Thus, for example, the oil phase may be at a higher temperature than the water phase. Vigorous mixing with a device such as a "Lightin" mixer will provide adequate agitation for emulsification. The product should be cooled after preparation. Fragrances, such as in the form of Perfume oil, can be added after emulsification, if desired, to prevent volatilization.

In practice, the compounds of the instant invention can be added to the oil phase. Depending upon the final desired pH of the finished product, they can be incorporated in either the acid or salt form. However independent of the pH of the final product, they can also be added to the oil phase in either the salt or acid form with the final adjustment of the pH being accomplished by the water phase.

The following examples are presented for the sole purpose of further illustrating the present invention and are not to be taken as limiting thereto. Unless otherwise specified, all parts and percentages are by weight.

EXAMPLE 1

(A) Preparation of α-methyl-butyrolactone-γ-carboxylic acid and its alkali metal salts Sodium α-methyl-butyrolactone-γ-carboxylate was prepared by reacting 180g of a 80 percent solution of lactic with a sufficient amount of KOH to convert the lactic acid to a potassium salt. An additional 30 grams of KOH and 3g of ZnO were then added to the resulting solution and the mixture was transferred to a liter Parr Bomb. The mixture in the bomb was brought to a temperature of 230° C. and was maintained there for about 6 hours. After cooling, the contents of the bomb were dissolved in water and were then acidified with a sufficient amount of HCl. The resulting solution was then concentrated by evaporation to yield a residue. To the residue, now contained in a flask, was added 200 ml of ethyl alcohol, 600 ml of benzene, a 3 ml of concentrated $H_2SO_4$. The flask was then fitted with a Dean-Stark trap and the solution was heated at reflux until the formation of water ceased. The contents of the reflux mixture was then washed with a solution of $Na_2CO_3$ which was followed by several water washings until the wash water was found to be neutral by pH paper. The resulting solution was then dried, concentrated and fractionally distilled (b.p. 130°-132° C. at 5.5 mm Hg). The resulting diester was then subjected to acid hydrolysis and the resulting lactone acid was converted to the monosodium salt by the addition of sufficient NaOH.

(B) Preparation of α-methyl-butyrolactone-γ-carboxylic acid and its alkali metal salts Sodium α-methyl-butyrolactone-γ-carboxylate was prepared by dissolving 1.2g (0.05 moles) of sodium metal in 100 ml of anhydrous methanol. To this solution was added 53g (0.4 moles) of dimethyl malonate with stirring. To the resulting solution, 20g (0.2 moles) of methyl methacrylate was added and the solution was heated at reflux with stirring for about 3½ hours. After the solution had been allowed to cool, it was transferred to a separatory funnel along with about 300 mls of ethyl ether. This solution was then extracted with a saturated NaCl solution until the extract was neutral to pH paper. The contents of the separtory funnel were then dried, concentrated and were ultimately fractionally distilled (b.p. 123°-125° C. at 3.5 mmHg). This fraction was then brominated in $CCl_4$ in the presence of light which was followed by acid hydrolysis. The resulting lactone acid was treated with a sufficient amount of NaOH to yield the compound in the corresponding salt form.

EXAMPLE 2

Preparation of the sodium salt of the succinic half acid esters of sucrose

The sodium salt of succinic half acid esters of sucrose was prepared by adding 25g (0.073 moles) of sucrose to 125 mls of pyridine in a reflux flack. The mixture was heated at reflux for a period of ½ hour whereupon 65g (0.65 moles) of succinic anhydride was added to the mixture and heating at reflux was continued for 2 hours. The resulting reaction mixture was then concentrated to yield a viscous residue which was then dissolved in water. About 69g (0.65 moles) of $Na_2CO_3$ was then gradually added to this solution. Upon completion of this addition, the solution was freeze dried whereupon the resulting dry material was extracted with anhydrous methanol with removal of insolubles by filtration. The sucrose succinates were then precipitated from the methanol by the addition of acetone and separated by filtration.

EXAMPLE 3

Water Uptake Comparison Data

The compounds of the instant invention were compared to several known humectants to evaluate their ability to uptake water. Samples of sodium α-methyl-butyrolactone-γ-carboxylate, sodium sucrose succinate (D.S. 3.9 ), (D.S. 4.3), and (D.S. 5.9) were weighed into watch glasses along with samples of various known humectants including sodium-2-pyrrolidone-5-carboxylate, sodium lactate, and glycerin. These samples were then transferred to controlled temperature/humidity chambers for a period of 24 hours. The exact temperatures and humidities tested are shown in Table 1. Weights of the salts both before and after storage in the chambers were recorded and percent uptake of water by the salts was determined by the resulting change in weights. The percent water absorbed is shown in Table 1.

As can be seen from the results, the compounds tested displayed approximately equal hydration potential at common temperature and humidities as compared with the known humectants. This data indicates that the compounds have humectant activity.

EXAMPLE 4

Stratum Corneum Moisturization

Stratum Corneum obtained from sacrificed guinea pigs by exposing the skin of said pigs to ammonia vapors for one hour was dried in a dessecator until traces of water were removed. Sections of the corneum were then cut into segments approximately 1"×½" in size. These sections

TABLE 1:

| Hydration studies at various temperatures and humidities | | | |
|---|---|---|---|
| | Temperature ° F. | Humidity % | % $H_2O$ Absorbed |
| Sodium-2-pyrrolidone-5-carboxylate | 72 | 22 | 4 |
| | 72 | 50 | 53 |
| | 72 | 87 | 290 |
| | 80 | 80 | 147 |
| Sodium lactate | 72 | 22 | 3 |
| | 72 | 54 | 49 |
| | 72 | 87 | 320 |
| Glycerin | 72 | 22 | 8 |
| | 72 | 54 | 49 |
| | 72 | 87 | 264 |
| Sodium-α-methyl-butyrolactone-γ-carboxylate | 72 | 22 | 3 |
| | 72 | 50 | 39 |

TABLE 1:-continued

| | Hydration studies at various temperatures and humidities | | |
|---|---|---|---|
| | Temperature °F. | Humidity % | % H₂O Absorbed |
| | 72 | 87 | 304 |
| | 80 | 80 | 147 |
| Sodium Sucrose Succinate (D.S. 3.9) | 72 | 22 | 5 |
| | 72 | 50 | 36 |
| Sodium Sucrose Succinate (D.S. 4.3) | 72 | 50 | 39 |
| | 80 | 80 | 119 |
| Sodium Sucrose Succinate (D.S. 5.9) | 72 | 54 | 28 |
| | 72 | 87 | 229 |
| | 80 | 80 | 96 | were then weighed on a micro balance to determine their weight. The sections were then returned to the dessecator for a period of 24 hours whereupon they were weighed again to determine if they have come to an equallibrium weight. This procedure was repeated until the weight of each section was constant. The sections were then placed on tared wire grids and were weighed again to obtain the starting weight of the stratum corneum. Individual sections on the wire grid were then placed in one percent by weight aqueous solutions of sodium-2-pyrrolidone-5-carboxlate, sodium-α-methyl-butyrolactone-γ-carboxylate, sodium sucrose succinate (D.S. 5.9). Additional sections were placed in a water placebo and others were reserved without treatment. Treatment time was 15 minutes of total immersion for each of the solutions. After the treatment, the sections (still on the wire grids) were placed in a dessicating chamber (0 percent relative humidity) for 24 hours to remove excess water. Following the drying, sections on the grids were weighed to determine weight after treatment. Whereupon they were transferred to a humidity chamber where they were allowed to stand for 24 hours. At intervals of 3, 6, and 24 hours, the sections were removed and weighed to determine water uptake. Water uptake was determined by subtracting post-treatment stratum corneum weight from the weight obtained at each of these subsequent weighings. Increases in weight were further adjusted by subtracting the value obtained on the untreated sections from the values obtained from the treated sections.

The results of this uptake study are shown in Table 2. As can be seen, the sodium-2-pyrrolidone-5-carboxlate treated stratum corneum adsorbed 8.3 percent to 14.3 percent of its own weight in water over a 24-hour period. The sodium-α-methyl-butyrolactone-γ-carboxylate adsorbed 1.5 percent to 9.3 percent over the same period. The sodium sucrose succinate (D.S. 5.9) adsorbed 4.3 percent to 15.6 percent of its weight of water during the same period of time. Additionally, it was shown that the water control adsorbed only from 0.2 percent to 3.5 percent of its weight for a similar period. This data indicates that the compound of the instant invention provide an emollient activity equivalent to that of the known sodium-2-pyrrolidone-5-carboxlate.

TABLE 2

| | Water Uptake by Stratum Corneum | | |
|---|---|---|---|
| | Water Uptake at 88% Rel. Humidity** | | |
| Treatment Agent* | 3 hr. | 6 hr. | 24 hr. |
| Sodium-2-pyrrolidone-5-carboxylate | 8.3% | 20.4% | 14.3% |
| Sodium-α-methyl-butyrolactone-γ-carboxylate | 1.5% | 9.7% | 9.3% |
| Sodium Sucrose Succinate (D.S. 5.9) | 4.3% | 11.8% | 15.6% |
| Water Placebo | 0.2% | 4.3% | 3.5% |

*1% Aqueous solution
**all values are given a % water uptake per unit weight of stratum corneum EXAMPLES 5a & b— Cold Cream

| | (a) Parts | (b) Parts |
|---|---|---|
| Beeswax (white) | 10.0 | 10.0 |
| Lanolin | 10.0 | 10.0 |
| Ethoxylated fatty alcohol (8–30 moles of ethylene oxide) | 5.0 | 5.0 |
| Paraffin Oil | 8.0 | 8.0 |
| Cetyl alcohol | 2.0 | 2.0 |
| Stearin | 1.0 | 1.0 |
| Fatty alcohol sulfate | 0.5 | 0.5 |
| Cholesterol | 0.5 | 0.5 |
| Triethanolamine | 0.5 | 0.5 |
| Sodium-α-methyl-butyrolactone-γ-carboxylate | 1.0 | — |
| Sodium sucrose succinate (D.S.≳5) | — | 1.0 |
| Water, Q.S. | | |
| Total | 100.0 | 100.0 |

These creams are useful in restoring dried skin caused by excessive use of cosmetic preparations such as mascara.

EXAMPLES 6a & b— A Skin Lotion

The following compositions are prepared, in which the parts by weight are as follows:

| | a Parts | b Parts |
|---|---|---|
| Oil Phase: | | |
| Stearic Acid | 18.00 | 18.00 |
| Mineral Oil | 5.00 | 5.00 |
| Polyoxyethylene (20) propylene glycol monostreate | 5.00 | 5.00 |
| Propyl ester of p-hydroxybenzoic acid | 0.05 | 0.05 |
| Water Phase: | | |
| Propylene glycol | 5.00 | 5.00 |
| Methyl ester of parahydroxybenoic acid | 0.10 | 0.10 |
| Sodium-α-methyl-butyrolactone-γ-carboxylate | 5.00 | — |
| Sodium Sucrose succinate (D.S. ≳5) | — | 5.00 |
| Sodium hydroxide | 1.60 | 1.60 |
| Water | 59.25 | 59.25 |
| Triethanolamine | 1.00 | 1.00 |

The materials in the oil phase are mixed with rapid agitation while heating them to a temperature of about 75° C. The previously mixed water phase is then added at about the same temperature while maintaining constant agitation. The mixture is then cooled to about 40° C. and agitation was slowed until the lotion reached room temperature. The resultant product is a free flowing lotion exhibiting moisturizing properties.

EXAMPLES 7a & b— Chapped Skin Cream

The following compositions are prepared in which the parts are by weight:

|  | a Parts | b Parts |
|---|---|---|
| Cetyl alcohol | 1.50 | 1.50 |
| Stearyl alcohol | 1.50 | 1.50 |
| Sodium lauryl sulfate | 0.25 | 0.25 |
| Polyethylene glycol laurate | 1.00 | 1.00 |
| Mineral Oil | 5.00 | 5.00 |
| Lanolin | 1.00 | 1.00 |
| Sodium-α-methyl-butyrolactone-γ-carboxylate | — | 5.00 |
| Sodium sucrose succinate (D.S.≳5) | 5.00 | — |
| Water Q.S. to 100 | | |

The active salts are dissolved in a small amount of the water, while the other ingredients are added to the remainder of the water and heated to 80° C. with continuous agitation. While the emulstion is cooling, the salt solution is incorporated and mixed continuously until room temperature is reached.

EXAMPLES 8a & b—Sun Tan Lotion

The following composition is prepared in which the parts by weight are:

|  | a Parts | b Parts |
|---|---|---|
| Glycerol monostearate | 2.0 | 2.0 |
| Stearic acid | 7.0 | 7.0 |
| Oleic acid | 3.0 | 3.0 |
| Cetyl alcohol | 2.0 | 2.0 |
| α-methyl-butyrolactone-γ-carboxylic acid | — | 2.0 |
| Succinic half acid ester of sucrose (D.S.≳5) | 2.0 | — |
| Triethanolamine | 0.9 | 0.9 |
| p-amino-benzoic acid | 4.0 | 4.0 |
| Water | 78.7 | 78.7 |
| Perfume | 0.4 | 0.4 |

The triethanolamine and the respective salts are dissolved in the water at a temperature of about 80° C. to form a solution. The remaining ingredients except for the perfume are melted and stirred together at about the same temperature after which the aqueous solution and the melt are mixed and stirred thoroughly while cooling. When the mixture cooled, the perfume is added. The resultant product is useful as a suntan aid.

Although specific embodiments of the invention have been disclosed herein, it is not intended to limit the invention solely thereto, but to include all of the obvious variations and modifications within the spirit and scope of the appended claims.

What is claimed is:

1. A moisturizing cosmetic composition comprising a water-in-oil emulsion and an amount effective to provide a moisturizing effect of a compound of the general formula,

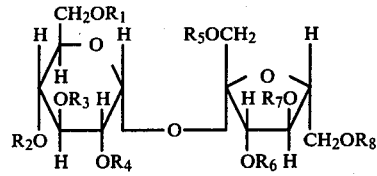

wherein $R_1$, $R_2$, $R_3$, $R_4$, $R_5$, $R_6$, $R_7$, and $R_8$, each may be either hydrogen; or of the general formula,

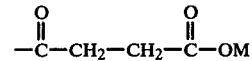

wherein M is hydrogen, sodium or potassium; or mixtures thereof; and wherein the average degree of esterification of said compound is at least about 62 mole percent.

2. The moisturizing composition according to claim 1, wherein said compound is present in said composition in an amount greater than one percent by weight of said composition.

3. The moisturizing composition according to claim 1, wherein the water-to-oil ratio of said emulsion is about 1:2 to about 3:1.

4. The moisturizing composition according to claim 1, wherein said composition further comprises an emulsifier consisting of lime water and stearic acid.

5. The moisturizing composition according to claim 4, wherein the water-to-oil ratio of said emulsion is about 1:1 to about 1:2 and which further comprises an emollient, a humectant and an emulsifier.

6. The moisturizing composition according to claim 5 wherein said emollient is selected from the group consisting of a wax ester, a steroid alcohol, a fatty alcohol, a triglyceride ester, a phospholipid, a polyhydric alcohol ester, a fatty alcohol ester, an alkyl fatty acid ester, a hydrocarbon oil or wax, a silicone oil, and mixtures thereof; said humectant is selected from the group consisting of glycerol, propylene glycol and sorbitol; and said emulsifier is selected from the group consisting of a fatty acid soap, a polyol fatty acid mono ester containing a fatty acid soap, a sulfuric ester, a polyol fatty acid mono ester containing a sulfuric ester, N (stearoyl colamino formylmethyl) pyridinium chloride, N-soya-N-ethyl morpholinium ethosulfate, an alkyl dimethyl benzyl ammonium chloride, (diisobutyl phenoxy ethoxy) ethyl dimethyl benzyl ammonium chloride, cetyl pyridinium chloride, a polyoxyethylene fatty alcohol ether, a polyoxyethylene fatty acid ester, a polyoxyethylene sorbitan fatty acid ester, a sorbitan fatty acid ester, a polyoxyethylene glycol fatty acid ester, a polyol fatty acid ester, and mixtures thereof.

7. A method of moisturizing skin comprising contacting said skin with the moisturizing composition of claim 1.

8. A method of moisturizing skin comprising contacting said skin with the moisturizing composition of claim 2.

9. A method of moisturizing skin comprising contacting said skin with the moisturizing composition of claim 5.

* * * * *